(12) United States Patent  (10) Patent No.: US 8,136,530 B2
Byrd et al.  (45) Date of Patent: Mar. 20, 2012

(54) CORRECTING MISSHAPED EARS

(76) Inventors: Henry Stephenson Byrd, Terrell, TX (US); C. Kenneth French, Cranfills Gap, TX (US); Garrett Barker, Meridian, TX (US)

( * ) Notice: Subject to any disclaimer, the term of this patent is extended or adjusted under 35 U.S.C. 154(b) by 916 days.

(21) Appl. No.: 12/113,452

(22) Filed: May 1, 2008

(65) Prior Publication Data

US 2009/0030358 A1 Jan. 29, 2009

Related U.S. Application Data

(60) Provisional application No. 60/951,388, filed on Jul. 23, 2007.

(51) Int. Cl.
*A61F 11/00* (2006.01)
*A61F 5/08* (2006.01)

(52) U.S. Cl. .................................. 128/864; 606/204.15

(58) Field of Classification Search .................... 623/10, 623/16, 11, 12; 128/846, 857, 864, 867, 128/868; 181/126, 128, 129, 130–135; 606/204.15, 606/201, 204, 120
See application file for complete search history.

(56) References Cited

U.S. PATENT DOCUMENTS

| 2,339,572 | A | * | 1/1944 | Jurovaty | ................. | 606/204.15 |
| 3,823,713 | A | | 7/1974 | Shah | | |
| 4,187,838 | A | | 2/1980 | Dubrowski | | |
| 5,295,950 | A | | 3/1994 | Godley | | |
| 5,433,748 | A | * | 7/1995 | Wellisz | ........................... | 623/10 |
| 5,615,417 | A | | 4/1997 | Jackson | | |
| 5,827,212 | A | | 10/1998 | Gaskill | | |
| 6,517,557 | B1 | | 2/2003 | Sorribes | | |
| 7,093,600 | B2 | | 8/2006 | Sorribes | | |
| 7,117,546 | B2 | * | 10/2006 | Goulding | .......................... | 2/423 |
| 7,799,075 | B2 | | 9/2010 | Kang et al. | | |
| 2004/0237175 | A1 | * | 12/2004 | Carrafield et al. | ................ | 2/423 |
| 2006/0184184 | A1 | | 8/2006 | Sorribes | | |

(Continued)

FOREIGN PATENT DOCUMENTS

WO WO2009-014908 A1 1/2009

OTHER PUBLICATIONS

Jou Hyun Park, M.D., et al. "Non-Operative Correction of Congenital Auricular Deformities Using a Silicone Splint," National Library of Medicine, Sep. 2000, vol. 27, No. 5, pp. 532-538.

(Continued)

*Primary Examiner* — Patricia Bianco
*Assistant Examiner* — Tarla Patel
(74) *Attorney, Agent, or Firm* — Fish & Richardson P.C.

(57) ABSTRACT

A system and method for correcting misshaped ears using a base section defining an opening dimensioned to accommodate the passage of the ear through the opening and a top section releasably engageable with the base section defining a compartment therebetween. A first stint can be arranged on an anterior surface of the base section to maintain a desired anatomic shape of the ear essentially in an area of the antihelix and the superior limb of the triangular fossa. A second stint can be placed in an area of the scapha of the ear to maintain a desired contour of the scaphal area. A conchal stint can be placed in the concha to maintain a desired anatomic shape of the concha. The top section can be engaged to maintain a desired amount of stabilizing pressure on the ear, the first stint, the second stint, and conchal stint.

12 Claims, 7 Drawing Sheets

U.S. PATENT DOCUMENTS

2008/0086067 A1    4/2008    Hay et al.

OTHER PUBLICATIONS

D J M MacDonald, et al., "Case presentation: a novel way of treating acute cauliflower ear in a professional rugby player," B J Sports Med, 2005 <URL:http://www.bjsportmed.com >.

Michael Miravet Sorribes, M.D., et al. "NonSurgical Treatment of Prominent Ears With the Auri Method," Arch Otolaryngol Head Neck Surg, Dec. 2002, vol. 128, pp. 1369-1376.

Swee T. Tan, MBBS, et al. "Molding Therapy for Infants with Deformation Auricular Anomalies," Annals of Plastic Surgery, Mar. 1997, vol. 38, No. 3, pp. 263-268.

S. T. Tan et al. "A Split for Correction of Congenital ear Deformities," British Journal of Plastic Surgery, Apr. 1994, vol. 47, No. 8, pp. 575-578.

J. Oroz, et al., "Congenital anomalies of the auricle: correction using external splints," European Journal of Plastic Surgery, 1995, vol. 18, pp. 288-292.

F. Schonauer, et al., "Splintage for correction of congenital ear deformities," European Journal of Plastic Surgery, Sep. 2003, vol. 26, pp. 290-293.

K. Matsuo, et al. "A Splint for Nonsurgical Correction of Cryptotia," European Journal of Plastic Surgery, 1989, vol. 12, pp. 186-187.

K. Matsuo, et al. "Nonsurgical Correction of Congenital Auricular Deformities in the Early Neonate: A Preliminary Report," Plastic and Reconstructive Surgery, 1984, vol. 73, pp. 38-50.

International Preliminary Report on Patentability issued in International Application No. PCT/US2008/069658, Jan. 26, 2010, 8 pages.

International Search Report and Written Opinion of the International Searching Authority issued in International Application No. PCT/US2009/036328, Feb. 23, 2010, 14 pages.

PCT/US08/069658 International Search Report and Written Opinion, PCT, Oct. 1, 2008.

N. Kurozumi, et al., "Non-surgical correction of a congenital lop ear deformity by splinting with Reston foam," British Journal of Plastic Surgery, 1982, 35, 181-182.

Kiyoshi Matsuo, M.D.., et al., "Nonsurgical Correction of Congenital Auricular Deformities," Clinics in Plastic Surgery, Apr. 1990, vol. 17, No. 2.

Yehuda Ullmann, M.D., et al., "Early Nonsurgical Correction of Congenital Auricular Deformities," Plastic and Reconstructive Surgery, Mar. 2002, vol. 109, No. 3, pp. 907-913.

Takatoshi Yotsuyanagi, M.D., Ph.D., "Nonsurgical Correction of Congenital Auricular Deformities in Children Older than Early Neonates," Plastic and Reconstructive Surgery, Jul. 2004, vol. 114, No. 1, pp. 190-191.

Ear Buddies™ Splints—How to fit Ear Buddies Splints, retrieved Nov. 11, 2008 from the internet. <URL: http://www.earbuddies.co.uk/pws/Content.ice?page=FIT&pgForward=content>, p. 1-6.

AuriClinic, Prominent ears treatment, retrieved Nov. 11, 2008 from the internet. <URL:http://www.auriclinic.com/clinic/prominent-ears-treatment/patented-method/.

AuriClinic, FAQ, retrieved Nov. 11, 2008 from the internet. <URL:http://www.auriclinic.com/clinic/faq, p. 1-5.

Swee Tan, et al., "Correction of deformational auricular anomalies by moulding-results of a fast-track service," The New Zealand Medical Journal, Sep. 2003.

International Preliminary Report on Patentability issued in international Application No. PCT/US2009/036328, mailed on Aug. 25, 2011, 8 pages.

Office Action issued in Chinese Patent Application No. 200880108740.X (translation included), May 11, 2011, 13 pages.

Communication pursuant to Article 94(3) EPC issued in international application No. 08 781 618.7-2310, Aug. 12, 2010, 6 pages.

* cited by examiner

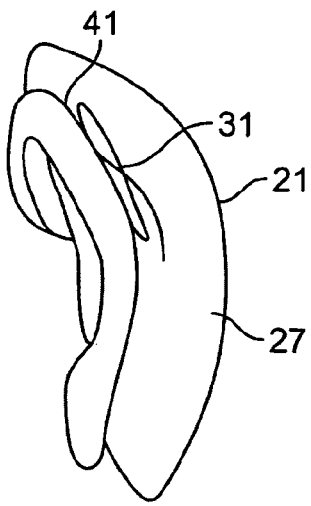
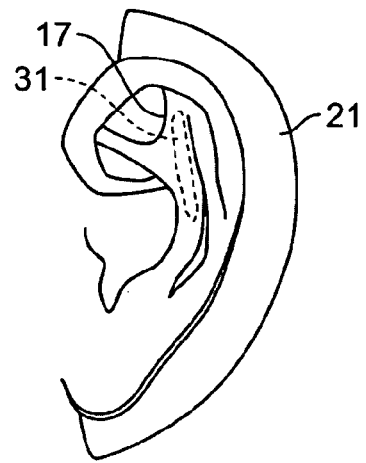
FIG. 4A  FIG. 4B
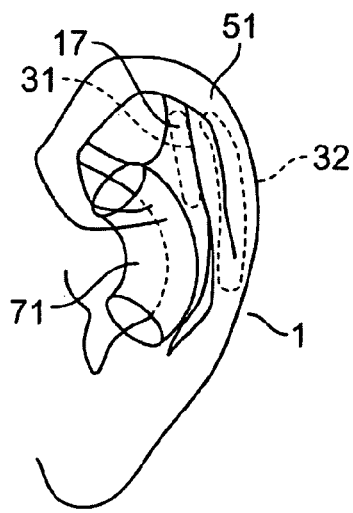
FIG. 5
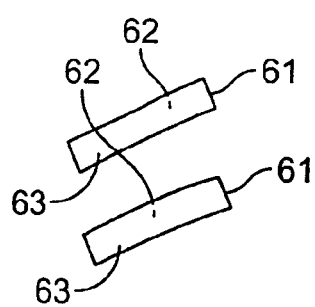
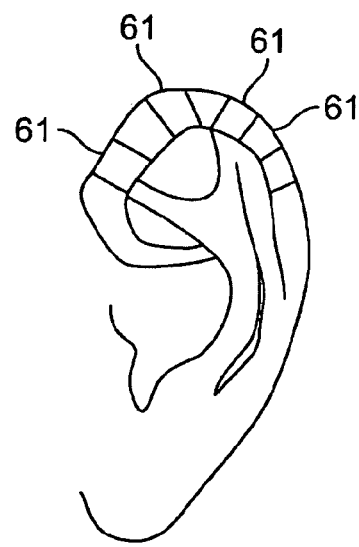
FIG. 6A  FIG. 6B

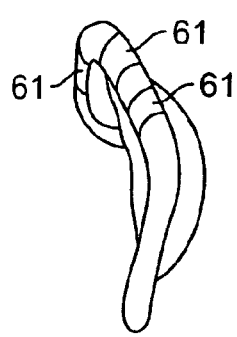
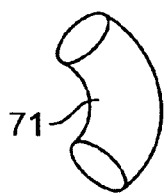
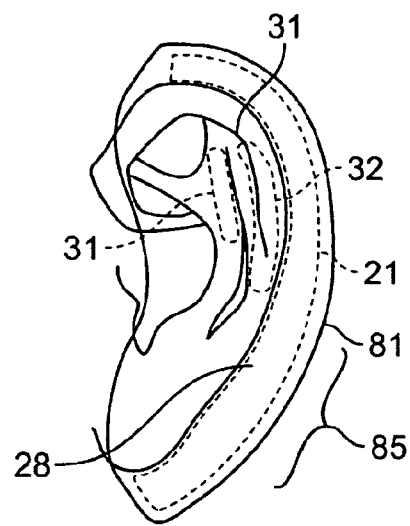
FIG. 6C      FIG. 7
FIG. 8A
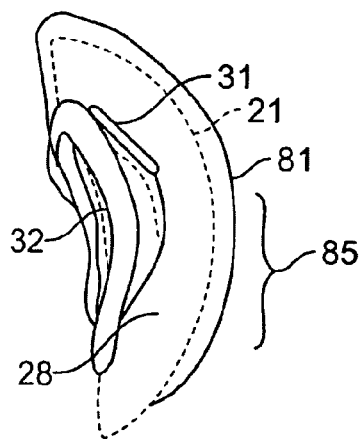
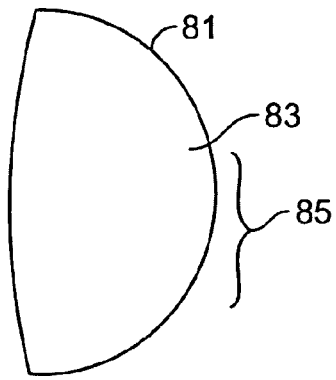
FIG. 8B
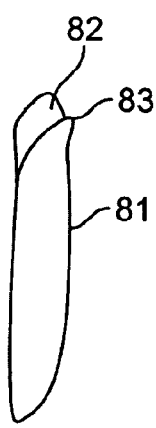
FIG. 8D
FIG. 8C

CORRECTING MISSHAPED EARS

CROSS-REFERENCE TO RELATED APPLICATIONS

This application claims priority under 35 U.S.C. §119(e) to U.S. provisional patent application Ser. No. 60/951,388, filed on Jul. 23, 2007, the entire contents of which are hereby incorporated by reference.

TECHNICAL FIELD

This invention relates to correcting misshaped ears, and more particularly to non-surgical correction of misshaped ears.

BACKGROUND

The ear consists of a complex arrangement of cartilage covered by skin, forming the characteristic shape of the ear (See FIG. 1). Some of the major structures of the ear are the helix, which is the outer most part of the ear and is characterized by a roll or rim (helical rim). The scapha (or scaphoid fossa) separates the helical rim from the antihelix which forms the defining curvature separating the scapha from the concha. The antihelix gives rise to a Y shaped structure having two crura. The two crura form the fork of the Y and merge into the body of the antihelix. The area between the two crura is the triangular fossa. The deep recess leading to the auditory canal is the conchal bowl. It has an oblique and vertical component. The vertical component contributes to ear projection and is continuous with the antihelix. Depending on the survey, there may be an incidence of misshapen or deformed ears in the newborn population of up to or greater than forty percent. A few among the various types of congenital auricular deformities are prominent ear, cup ear, lop ear, Stahl's ear, conchal crus, misshapen ears, helical rim compression, and Tanzer I-II constricted ear.

Prominent ear is an ear in which the helical rim projects more than 15-18 mm from the mastoid in an adult and more than 5 mm in an infant. Cup ear is characterized by incomplete curvature or formation of the antihelix and superior limb of the triangular fossa, and without the normal curve of these structures, the ear "cups" forward. Lop ear is characterized by a "lidding" or folding over of the superior third of the ear. Stahl's ear, also called "Spock" ear, is characterized by a "transverse crus" extending off the Y of the antihelix, deforming the natural curve of the helical rim and causing the ear to have a point like an elf's ear. Conchal crus is an abnormal crus or fold that extends across the oblique portion of the conchal floor to the vertical conchal wall, appearing to divide the ear in half at the level of the external auditory canal. Misshapen ears are variations of malformations of the auricular cartilage that do not fit into the above defined categories. These ears may appear to be "crinkled", folded, or collapsed in varying parts of the framework. Helical rim compression is characterized by an inward buckling of the rim disturbing its normal curvilinear contour. Tanzer I-II constricted ears have increasingly severe grades of skin and/or cartilage absence or deficiency. In Tanzer I ears, the helical rim is rolled-in as there is a shortage or deficiency of skin along the inner rim that prevents the helical rim from being rolled out. With Tanzer II, the deficiency is greater and actually affects the scaphal cartilage as well. Both surgical and non-surgical means have been used in an attempt to correct these and other deformities of the ear.

SUMMARY

Techniques are described for non-surgical correction of misshapen ears. Although various types of misshaped ears present at birth may involve deformities of one or more anatomic structures of the ear, the techniques presented below can be tailored to correct deformities of the one or more anatomic structures. Some of the anatomic structures of the ear of interest are an antihelix, a superior limb of the triangular fossa, a helical rim, a concha, and a scapha area.

In one general aspect, a splint system for an ear has a biocompatible material with a first adhesive surface and a second adhesive surface. The biocompatible material is shaped to facilitate placement of the first adhesive surface posterior to the ear on a retroauricular skin surface. A first splint is adapted for placement between the ear and the retroauricular skin surface to maintain a desired anatomic shape of the ear in an area of the antihelix and the superior limb of the triangular fossa. A second splint is adapted for placement in an area of the scapha of the ear, the second splint maintaining a desired contour of the scaphal hollow. An anterior adhesive cover is designed to fit over the ear. The anterior adhesive cover covers at least a portion of the second splint and adheres to the biocompatible material in at least one region.

In another general aspect, a method of correcting a misshaped ear is presented. The method involves placing a biocompatible material, having a first adhesive surface and a second adhesive surface, on a retroauricular skin surface posterior to the ear such that the biocompatible material is secured to the retroauricular skin by the first adhesive surface. A first splint is applied to the second adhesive surface in a position corresponding essentially to an area of the antihelix and the superior limb of the triangular fossa. An underneath surface of the ear is tacked down to the second adhesive surface and over the first splint, such that the first splint facilitates a desired anatomic configuration of the ear in the area. A second splint is inserted into the anterior scaphal area of the ear, such that the second splint maintains a desired contour of the anterior scaphal area. At least a portion of the second splint is secured in place with an anterior adhesive cover having a single adhesive surface.

In another general aspect, a method of treating deformities of the ear is presented. The method involves assessing an ear having deformities. A strip of tape, having adhesive on one side, can be wrapped from an area of the ear infero-medial to the helical rim over the helix to an area on the underneath aspect of the ear when an area of the helical rim is lidded over. An adhesive unit, having a first and second adhesive surface, can be applied by adhering the first adhesive surface to a retroauricular skin surface behind the ear. A first stint can be positioned, when there is a deformity of the superior crus, such that the first stint extends essentially from the antihelix to the helical rim on an underneath surface of the ear. The first stint is molded to recreate the superior crus. The underneath surface of the ear can be rolled over the first stint, if present, and onto the second adhesive. When there is a deformity of the scapha, a second stint molded to provide a desired anatomy of the scapha can be placed into an area of the scapha without overlapping the first stint, if present. When there is a deformity of the concha, a conchal stint molded to provide a desired anatomy of the concha can be inserted into an area of the concha. The ear can be covered with a cover, having a single adhesive surface, such that the single adhesive surface covers a portion of one or more of the stints, and at least a portion of the second adhesive surface.

In another general aspect, an ear molding system for an ear is presented. The ear molding system includes a base section having an opening through which the ear is passed such that the ear is positioned within the base section. The base section has a posterior surface, an anterior surface and a rim positioned on and projecting anteriorly from the anterior surface. The system has a first splint adapted for placement between the ear and the anterior surface in a position to maintain a desired anatomic shape of the ear in an area of the antihelix and the superior limb of the triangular fossa. The system has a second splint adapted for placement in an area of the scaphal area of the ear, the second splint maintaining a desired contour of the scaphal area. The system also has a cap adapted to reversibly attach to the rim such that the cap covers the ear, applying a stabilizing pressure to the ear and the first and second splints.

In another general aspect, a molding device for a human ear includes a base section, a top section, and a first stent. The base section includes a posterior surface and an anterior surface, and defines an opening dimensioned to accommodate the passage of the ear through the opening. The top section is releasably engagable with the base section, and a compartment is defined between the top section and the base section. The stent is arranged on the anterior surface and is adapted to maintain a desired anatomic shape of the ear in an area of the antihelix and the superior limb of the triangular fossa.

Implementations may include one or more of the following features. The first stent of a molding device can be integrally formed with the base section. The molding device may include a second stent adapted for placement in the scaphal area of the ear. The second stent can be further adapted to maintain a desired contour of the scaphal area. In some implementations, the top section of the molding device is adapted to apply a stabilizing pressure to the ear, the first stent, and the second stent. A surface of the second stent may be tacky. The molding device may include a conchal stent adapted for placement in the concha of the ear to maintain a desired anatomic shape of the concha. The conchal stent can have a half-moon shape adapted for placement around a back wall of the concha, such that pressure applied by the top section facilitates maintenance of the desired anatomic shape of the concha. The molding device may further include a pad adapted for positioning between the conchal stent and the top section. The pad can also be adapted in combination with the top section to provide a stabilizing pressure to the conchal stent.

In some implementations, the molding device further includes a strip of biocompatible material with a first adhesive surface and a second adhesive surface. The strip is shaped to facilitate placement of the first adhesive surface of the strip on the anterior surface of the base section in a position to facilitate placement of an area of skin on a posterior aspect of the ear between the base of the ear and the helical rim over the first stent and on the second adhesive surface of the strip.

The posterior surface of the base section may include an adhesive material on the posterior surface adapted to adhere the posterior surface to a retroauricular skin surface. In some implementations, a biocompatible material, having a first adhesive surface and a second adhesive surface, is shaped to facilitate placement of the first adhesive surface posterior to the ear on a retroauricular skin surface, and placement of the posterior surface of the base section on the second adhesive surface.

A biocompatible wrap-around material or adhesive strip, having a single adhesive surface, is adapted so that one end can be positioned using the single adhesive surface on the ear in an area infero-medial to the helical rim. The wrap-around material can then be wrapped around the helix and the other end can be secured to the skin on a posterior aspect of the ear to expand the skin in the infero-medial area.

The wrap-around material can be formed using one or more strips having rectangular dimensions. For example, the dimensions can be approximately ¼ of an inch by approximately ½ of an inch. The wrap-around material is formed using a porous material adapted to allow the skin beneath to breathe during use. The wrap-around material is formed using a transparent material adapted to aid in detection of ischemia and infection of the skin underneath during use.

A conchal splint is adapted for placement in the conchal area of the ear to maintain the desired anatomic shape of the concha. In some implementations, the conchal split has a half moon shape adapted for placement around a back wall of the concha. The conchal splint has a height sufficient to project beyond the surface of the ear allowing pressure to be applied specifically to the conchal hollow. The pressure can be applied by the anterior adhesive cover and/or the cap. The conchal splint can be molded to a shape that facilitates the correct anatomic shape of the ear.

The biocompatible material is formed using a transparent material adapted to aid in the detection of ischemia and infection of the skin underneath during use. The biocompatible material is formed using a porous material adapted to allow the skin underneath to breathe during use. A first and a second cover adapted to cover the first and second adhesive surfaces, respectively, prevent adhesion of the first and second adhesive surfaces to other surfaces prior to their respective covers being removed. The second adhesive surface is adapted to allow the first splint to be placed upon the second adhesive surface and held in place prior to a positioning of the ear onto the second adhesive surface. The second adhesive surface is adapted to adhere to an underneath surface of the ear, allowing the ear to be tacked down to the retroauricular skin surface to achieve a desired molding of the ear. The biocompatible material can be provided in a variety of dimensions to facilitate placement on the retroauricular surface posterior to and around the base of the ear.

One or more of the splints have a tacky surface material covering their respective surfaces that aids in positioning of the splint. The first splint is essentially cylindrical in its longitudinal dimension and moldable to splint the ear in the desired anatomic shape. The second splint is essentially cylindrical in its longitudinal dimension and moldable to splint the ear to maintain the desired contour of the scaphal area.

The anterior adhesive cover can be shaped to cover one or more splints used to correct a deformity of the ear and to cover the exposed second adhesive surface. The anterior adhesive cover is formed using a transparent material. The anterior adhesive is formed using a porous material adapted to allow the skin to breathe.

The posterior surface of the base section can have an adhesive material thereon to facilitate attachment to a retroauricular skin surface. A biocompatible material having a first adhesive surface and a second adhesive surface can be attached using the first adhesive surface to a retroauricular skin surface and the second adhesive surface can be attached to the posterior surface of the base section securing the posterior surface to the retroauricular skin surface when there is no adhesive material on the posterior surface.

The biocompatible material can be shaped to conform to the posterior surface of the base section, such that the first adhesive surface adheres to the skin surrounding the ear and the second adhesive surface adheres to the posterior surface.

A bladder can be positioned between the cap and the ear such that the bladder contributes to the stabilizing pressure on at least a portion of the ear. At least a portion of the cap has a mesh or holes allowing visualization of the ear and the base section. The base section, the cap, and/or the mesh can be made using polypropylene.

In another general aspect, a method of correcting a misshaped ear includes positioning the ear within a compartment defined between a bottom section and a top section, locating a first splint in a position substantially corresponding to an area of the antihelix and the superior limb of the triangular fossa, and placing a posterior aspect of the ear between the base of the ear and the helical rim over the first splint. The top section is releasably engageable with the bottom section. The bottom section has an anterior surface, a posterior surface, and an opening dimensioned to accommodate the passage of the ear. The first splint is arranged on the anterior surface of the bottom section. The posterior aspect of the ear between the base of the ear and the helical rim is placed over the first splint such that the first splint facilitates a desired anatomic configuration of the ear in the area of the antihelix and the superior limb of the triangular fossa. Implementations may include one or more of the following features. The method may include securing the posterior aspect of the ear to the anterior surface. Securing of the posterior aspect of the ear to the anterior surface includes securing a first adhesive surface of a strip of biocompatible material onto the anterior surface in an area corresponding to an area of skin on the posterior aspect of the ear between the base of the ear and the helical rim, and rolling the area of skin over the first splint and securing the area of skin to a second adhesive surface of the biocompatible material.

In some implementations, the method includes inserting a second splint into the scaphal area of the ear, such that the second splint maintains a desired contour of the scaphal area. A conchal splint may be placed in a area of the concha to facilitate a correct anatomic shape of the ear in the area of the concha. In certain implementations, the method includes placing a pad between the ear and the top section. The pad facilitates maintaining a desired amount of pressure on the conchal splint when the top section is engaged.

In some implementations, a method of correcting a misshaped ear further includes applying a first end of an adhesive strip to an area of skin infero-medial to the helix, wrapping the adhesive strip around the helix, and securing a second end to an area of skin on a posterior aspect of the ear between the base of the ear and the helical rim. The adhesive strip has adhesive only on a single surface. The second end is secured such that tension is applied to the area of skin infero-medial to the helix.

The method may further include securing the posterior surface of the bottom section onto at least a portion of a skin surface surrounding the base of the ear. The top section can be engaged with the bottom section, and a desired amount of stabilizing pressure is applied on the ear and to the first and second splints. A pad that facilitates maintaining the desired amount of stabilizing pressure on the ear and the first and second splints may be placed between the top section and the ear.

The details of one or more implementations are set forth in the accompanying drawings and the description below. Other features will be apparent from the description and drawings, and from the claims.

DESCRIPTION OF DRAWINGS

FIG. 4A is a view looking at the ear from a posterior to anterior direction showing an implementation having a double adhesive element placed behind the ear on the retroauricular skin with a posterior stint positioned thereon;

FIG. 4B is a view of the ear from a lateral perspective showing a double adhesive element positioned behind the ear and a posterior stint positioned thereon;

FIG. 5 is a view of the ear from a lateral perspective showing relative positions of a posterior stint, an anterior scaphal stint and a conchal stint;

FIG. 6A is a view of one implementation of a wrap-around material;

FIG. 6B is a view from a lateral perspective of the ear showing a wrap-around material applied to the helix of the ear;

FIG. 6C is a view from the posterior to the anterior of the ear having a wrap-around material applied to the helix;

FIG. 7 depicts one implementation of a conchal stint;

FIG. 8A is a view of the ear from a lateral perspective showing an application of a double adhesive element, a posterior stint, an anterior stint, and a single adhesive element;

FIG. 8B is a view of the ear from a lateral perspective showing an application of a double adhesive element, a posterior stint, an anterior stint, and a single adhesive element;

FIG. 8C shows a two dimensional view of one implementation of a single adhesive element;

FIG. 8D shows a side profile of a single adhesive element;

Like reference symbols in the various drawings indicate like elements.

DETAILED DESCRIPTION

Figure 1:
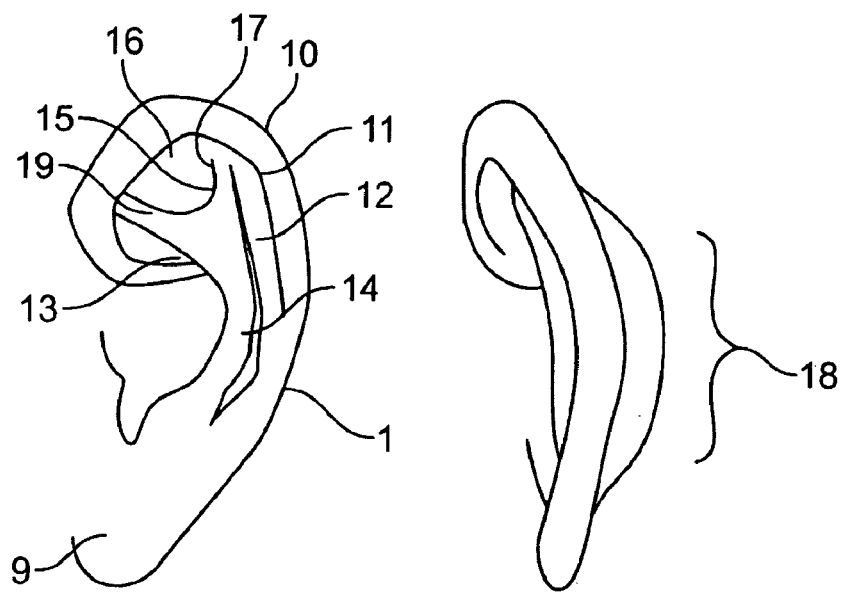
FIG. 1 is an anatomical drawing showing the major structures of an ear.

As shown in FIG. 1, an ear 1 has a very complicated structure, composed of cartilage covered by skin. Deformities involving various structures of the ear occur causing the ear to appear misshaped. The following structures are some of the structures of interest when discussing misshaped ears. Progressing generally from peripheral to central regions of the ear, the structures of interest are a helix 10, having a helical rim 11. A scaphoid fossa (scapha) 12 is located between the helical rim 11 and an antihelix 14. The antihelix 14 has a crura 15 forming a superior limb (superior crus) 17 and an inferior limb (inferior crus) 19 of a triangular fossa 16. A concha 13 is located in an area inferior to the inferior limb of the triangular fossa. An ear lobe 9 hangs down from the ear, inferiorly. A retroauricular skin surface 18 can be seen from a posterior view as extending from the base of the ear.

Abnormalities of one or more of these structures result in ear deformities, such as prominent ear, cup ear, lop ear, Stahl's ear, conchal crus, misshapen ears, helical rim compression, lidding, and Tanzer I and II constricted ear. A non-surgical approach to the correction of these and other deformities of the ear can be accomplished using one or more of the following components of a system for correcting misshaped ears.

Figure 2A:
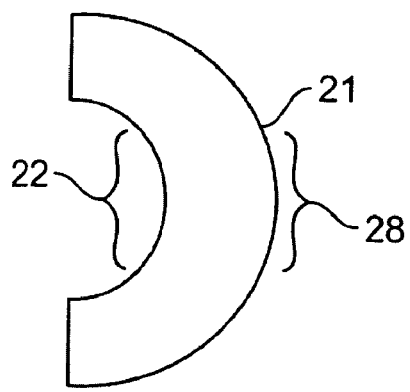
FIG. 2A is a two dimensional view of a double adhesive element.
Figure 2B:
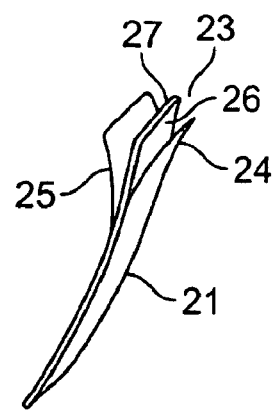
FIG. 2B is a side profile view of the double adhesive element of FIG. 2A.

As shown in FIG. 2, a double adhesive element 21, having a first adhesive surface 26 and a second adhesive surface 27, is sized and shaped to be placed on the skin of the retroauricular skin surface 18 in a position posterior to (or behind) the ear 1, as shown in FIGS. 4A and 4B. The double adhesive, element 21 can be provided as a sheet of material, which is cut to the desired dimensions, or provided in a range of sizes and shapes designed to accommodate the various ear dimensions encountered in the neonate and infant population. In some implementations, by using a ruler or caliper, the proper size of the double adhesive element can be selected and/or dimensioned, such that the inner curvature 22 fits behind/posterior to the ear around its base on the retroauricular skin surface 18, and the outer curvature 28 is greater than the dimensions of the peripheral ear, allowing the ear to be tacked down to the second adhesive surface 27 as shown in FIG. 4B. In other implementations, various sizes of prefabricated double adhesive elements can be measured against the desired coverage area, allowing for selection of an appropriately sized element. Although depicted in the figures as having a certain size and shape, any size and shape of the double adhesive element 21 that allows the ear to be tacked down and secured in the desired position to correct the deformity can be used.

In some implementations, the double adhesive element 21 can be made from a biocompatible material formable into a structure having an outer curvature 28 and an inner curvature 22. For example, the biocompatible material can be a polymer, such as polyethylene. The element 21 is shaped such that the inner curvature 22 fits behind/posterior to and around the base of the ear, as shown in FIGS. 4A and 4B. The adhesive on the first and second adhesive surface can be any biocompatible adhesive having a low incidence of causing skin allergy, irritation, and/or infection, such as an acrylate adhesive. By using materials for the double adhesive element 21 and the adhesive that have these properties, the double adhesive element 21 can remain adhered to the skin for a long duration. Thus, frequent changes, which may cause the skin to blister, are minimized. In some implementations, the element 21 is formed from a transparent material allowing visual access to the skin adhered to the first adhesive side 26. In some implementations, the element is made from a porous material allowing the skin beneath the double adhesive element 21 to breathe. Examples of materials that can be used for the double adhesive include 3M™ tape products 9917 or 1522.

The first adhesive surface and the second adhesive surface are covered by a first adhesive cover 24 and a second adhesive cover 25, respectively. The covers can be made of any material that isolates the adhesive and allows handling of the double adhesive element 21 for sizing and shaping if necessary, for example a plastic or paper film. The covers can be made from any material that allows some flexibility of the double adhesive element 21 during application, such that the element with one cover still attached is moldable to the skin surface contours. The covers are easily removable during application of the double adhesive element 21 to the retroauricular skin surface 18.

After selection of the appropriate size and shape, the double adhesive element 21 is applied by removing the first cover 24, then placing the first adhesive surface 26 in contact with the retroauricular skin surface behind/posterior to the ear. The second cover 25 facilitates placement of the element 21 by helping to maintain the shape of the element 21 and by providing an adhesive free surface for handling during placement. After placement in the desired position, the second cover 25 is removed exposing the second adhesive surface 27. Then, the skin on the underneath side (posterior aspect of the ear between the base of the ear and the helical rim) of the ear 1 can be positioned on the second adhesive surface 27 such that the ear is held in a desired position by the second adhesive surface 27. In some implementations, if correction of a superior crus 17 deformity is required, a posterior fossa stint 31 can be positioned on the second adhesive surface prior to the application of the ear on the second adhesive surface.

Figure 3A:
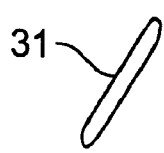
FIG. 3A depicts one implementation of a posterior fossa stint.

As shown in FIG. 3A, a posterior fossa stint (stent/splint) 31 is made out of a biocompatible material having a low allergenicity, such as flexible polyvinyl chloride. The posterior stint 31 is used to correct the shape of the ear the area of the superior crus 17, when there is a malformed or missing superior crus. In some implementations, the stint is manufactured in a variety of sizes (i.e. lengths and diameters). For example, the length can be between about ⅜" and ¾", preferably ½", and the diameter can be between about 6-12 French, preferably 8-10 French, and shapes, which allow a person, applying the posterior stint 31, to select an appropriately sized and shaped posterior stint to achieve the desired correction of the anatomic deformity of the ear 1. The shape of the stint, as viewed from a cross-section through the longitudinal axis of the stint, can be a circle, an oval, a polygon, a semi-circle or any other geometric shape that enables correction of the anatomic deformity without causing pressure necrosis. Thus, if the cross-sectional shape of the stint is a circle, then the stint is essentially cylindrical in shape, although either or both ends of the stint can be rounded to reduce acute edges that might damage the over or underlying skin. In other implementations, the posterior stint 31 is manufactured in different sizes (i.e. lengths and diameters), which are moldable into a desired shape for correction of the anatomic deformity of the ear. The posterior stint 31 can be covered with a tacky surface material, such as a siliconized surface having a natural adherence that allows for precise placement.

As shown in FIGS. 4A and 4B, the posterior stint 31 is designed for placement between the underneath skin surface of the ear and the retroauricular skin surface on the second adhesive surface 27. The posterior splint 31 is placed on the second adhesive surface 27 (see FIG. 4A) such that, when the ear is positioned over the stint on the second adhesive surface 27, the posterior stint 31 (depicted in FIG. 4B with dashed lines indicating that it is underneath the ear) extends essentially from the antihelix to the helical rim and shapes the ear by providing a desired shape of the missing superior crus of the antihelix. This stinting allows the ear 1 to reshape itself into an ear 1 having a more normal appearing superior crus 17. After tacking the ear 1 down to the second adhesive surface 27 and over the posterior stint 31 (if necessary), an anterior scaphal stint 32 can be placed in an area of the scapha to correct an anatomic deformity thereof, if present.

Figure 3B:
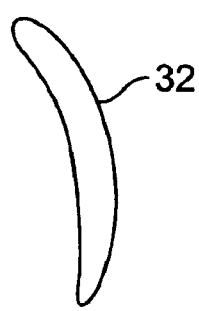
FIG. 3B depicts one implementation of an anterior scaphal stint.

The anterior scaphal stint (stent/splint) 32 shown in FIG. 3B can be made out of a biocompatible material, for example flexible polyvinyl chloride, and is designed to correct the shape of the ear when there is abnormal anatomy in the area of the scapha 12. In some implementations, the stint is manufactured in a variety of sizes (i.e. lengths and diameters) and shapes, which allow the person, applying the anterior stint 32, to select an appropriately sized and shaped anterior stint to achieve the desired correction of the anatomic deformity of the ear 1. The shape of the stint, as viewed from a cross-section through the longitudinal axis of the stint, can be a circle, an oval, a polygon, a semi-circle or any other geometric shape that enables correction of the anatomic deformity without causing pressure necrosis of the skin. The stint has a longitudinal curvature approximating the curvature of the scaphoid fossa, and either or both ends of the stint can be rounded to reduce acute edges that might damage the over or underlying skin. The stints can be manufactured having varying amounts of curvature allowing selection of a stint having a shape desired for correction of the anatomic deformity of the ear. In other implementations, the anterior stint 32 is manufactured in different sizes (i.e. lengths and diameters), which are moldable into the shape desired for correction of the anatomic deformity of the ear. The length of the anterior stint can be, for example, between about 1.5 cm to about 2.5 cm, and the diameter can be, for example, between about 10 to 12 French. The anterior stint 32 can be covered with a tacky surface material that allows more precise placement, for example a siliconized surface.

As shown in FIG. 5, the anterior stint 32 is placed in an area of the scaphoid fossa 12 for purposes of correcting an anatomic deformity. The anterior stint 32 is positioned such that there is no overlap with the posterior stint 31 in area 51, thus preserving the shape of the superior crus 17 and preventing an ischemic injury from developing in tissue compressed between the two stints. The anterior stint 32 is held in place by a single adhesive element 61 (shown in FIGS. 8A-8D).

As shown in FIG. 6A, a wrap-around material 61 has an adhesive surface 62 on one side and an opposite surface 63 lacking adhesive properties. Although not shown, adhesive surface 62 can be covered by a material having a non-adhesive surface from which the wrap-around material is peeled before application. One end of the adhesive surface 62 is applied to the skin in the area of the ear inferior and medial to the helical rim over the interior surface of the helix in areas where the helical rim is lidded over. Then, the wrap-around material 61 is wrapped around the helical rim and secured to the posterior aspect of the ear using the other end of the adhesive surface 62 to expand the skin and/or cartilage of the ear in the inferomedial area, allowing the lidded over area to be corrected into a more normal shaped helical rim. In some implementations, one or more strips of the wrap-around material are used in areas where the helical rim is lidded over. The wrap-around material 61 can also be applied to the helical rim or other parts of the ear and tacked down to the second adhesive surface 27 to contour the ear depending on the deformity being corrected.

The wrap-around material 61 is made from a biocompatible material and has a biocompatible adhesive. The wrap-around material 61 can be either a porous or non-porous material. Making the wrap-around material 61 from a porous material allows the skin beneath to breathe. By using wrap-around materials that allow the skin to breathe and that have low allergenicity, the wrap-around material 61 can be applied for a long duration, avoiding frequent changes that can irritate the skin and cause blistering. For example, the wrap-around material can be a clear wound closure strip or a MICROPORE™ surgical tape or an adhesive STERI-STRIP™, such as manufactured by 3M™, or a material having similar properties. The wrap-around material 61 has a size and shape that allows it to be conveniently wrapped around the helical rim to correct deformities thereof, for example the shape and size of the wrap-around material 61 can be a rectangle having the dimensions of between about ⅛ to ¼ of an inch wide, for example ¼" wide, and between about ½ to ¾ of an inch long, for example ½" long, although other sizes and shapes can be used. The wrap-around material 61 can also be supplied as a sheet of material, which is cut to the desired size and shape.

In some implementations, the wrap-around material 61 is not transparent. In other implementations, the wrap-around material 61 is transparent. Making the wrap-around material 61 transparent allows a person, applying the wrap-around material 61 to the ear, to observe the skin for blanching, if the tension applied by wrapping the wrap-around material 61 around the helical rim is too great. The blanching indicates that blood flow to the area is being restricted and can result in a blister. However, by using a transparent wrap-around material 61, this blanching can be observed and the wrap-around material 61 can be adjusted about the helical rim to decrease the tension. After application to the ear 1, any exposed areas of the wrap-around material 61 can be covered by a single adhesive element 61 (as shown in FIGS. 8A-8D).

As depicted in FIG. 7, a conchal stint/mold 71 is a shapeable, coated stint. The conchal stint, when viewed on end, has a generally curvilinear shape, such as an oval (other shapes can be used as long as they are dimensionally similar and there are no edges contacting a skin surface that might cause pressure necrosis), with a height of between about 5-10 mm, for example 7 mm, and a width between about 3-5 mm, for example 3 mm. The length of the stint is between about 12-17 mm, for example 15 mm and molded longitudinally into a half-moon curve to fit the back wall of the concha. The conchal stint serves to compress/flatten the conchal crus, which is crossing the oblique floor of the concha and disturbing the vertical wall and antihelix. Other shapes can be used as long as the mold is designed to fit around the back wall of the concha and compresses the conchal crus without causing pressure necrosis, i.e. a desired amount of pressure can be applied to the mold to compress the conchal crus. The stint can be made out of a biocompatible material, such as flexible polyvinyl chloride.

As shown in FIGS. 8C-8D, the single adhesive element 81 has a single adhesive surface 82, which is covered by a single adhesive cover 83. Opposite the single adhesive surface is a non-adhesive surface 84. Both the single adhesive element and the adhesive are made from biocompatible materials with low allergenicity. The single adhesive element 81 can be made from materials such as polymers like polyethylene or polyurethane. For example, single adhesive element can be wound dressing such as TEGADERM™ made by 3M™ and IV3000™ by SMITH and NEPHEW™. The single adhesive surface 82 is covered with an adhesive such as an acrylate adhesive. In some implementations, the single adhesive element 81 is porous allowing the skin beneath the surface to breathe. In other implementations, the single adhesive element is non-porous. In some implementations, the single adhesive 81 is non-transparent. In other implementations, the single adhesive element 81 is transparent allowing for inspection of the ear beneath for infection, allergic reaction, ischemia, and/or malposition of the stints and/or the ear. By using the single adhesive element 81 that allows the skin to breathe and that has a low allergenicity, the single adhesive element 81 can be applied for a long duration, avoiding frequent changes that can irritate the skin and cause blistering.

Opposite the single adhesive surface is a non-adhesive surface 84, which provides a non-adhesive surface for handling the single adhesive element 81, and which provides a non-adhesive covering for the ear. Although the single adhesive element can be formed in any shape and/or cut to conform to the desired shape, in some implementations a variety of sizes are provided having a semi-circular shape. By using a caliper or a ruler, the size of the ear 1 can be measured and the correct size of the single adhesive element 81 is chosen from a selection of pre-dimensioned elements or is cut to a desired shape from a sheet of material.

As shown in FIGS. 8A-8B, the single adhesive element 81 is cut or selected to have a size such that the radius of a curvature 85 is slightly greater than the radius of the outer curvature 28 of the double adhesive element 21. Then, after removing the single adhesive cover 83, the single adhesive element 81 is placed in a position similar to that shown in FIGS. 8A-8B, covering at least a portion of the ear where either or both the conchal and/or the anterior scaphal stint 32 are positioned, such that the single adhesive element 81 holds both the ear and the stint(s) in a desired position to correct the deformity, while providing pressure on the conchal stint to facilitate the compression or flattening of the conchal crus. In some implementations, by sizing the single adhesive element 81 to have a slightly greater radius than the double adhesive element, the single adhesive element 81, after being placed over the outer ear, is secured to the second adhesive surface 27, which is not covered by the tacked down ear. By adhering the portion of the single adhesive surface 82 not adhered to the ear to the second adhesive surface 27, the entire adhesive surface of the second adhesive surface 27 is covered. The single adhesive element forms an outer adhesive cover over the ear and other components of the stint system. Other sizes and shapes of both the single adhesive element 81 and the double adhesive element 21 can be used as long as they hold the ear and the stints in their respective positions desired for correction the misshaped ear.

Figure 10A:
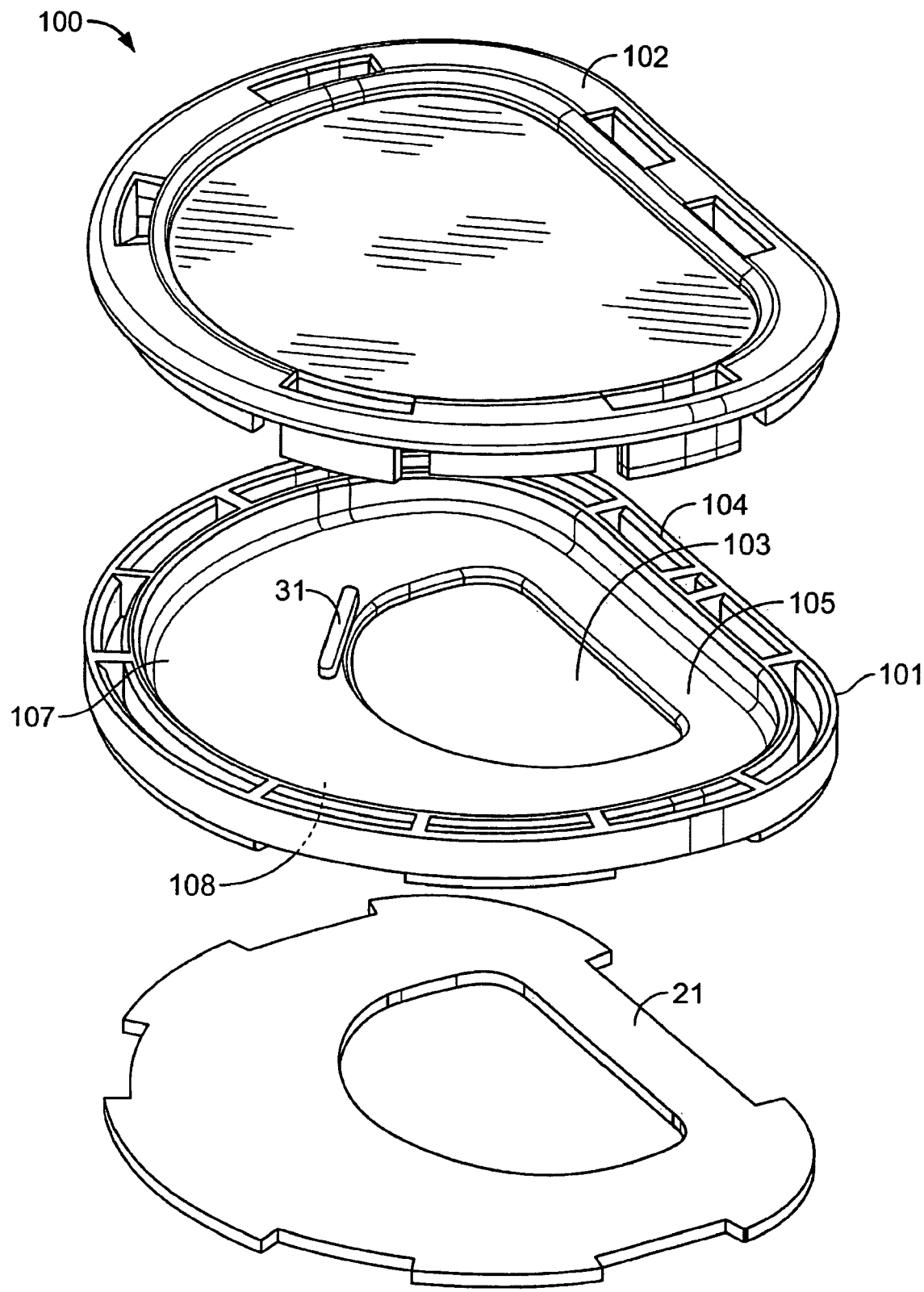
FIG. 10A is an exploded view of a clam shell with a bottom section and a top section.
Figure 10B:
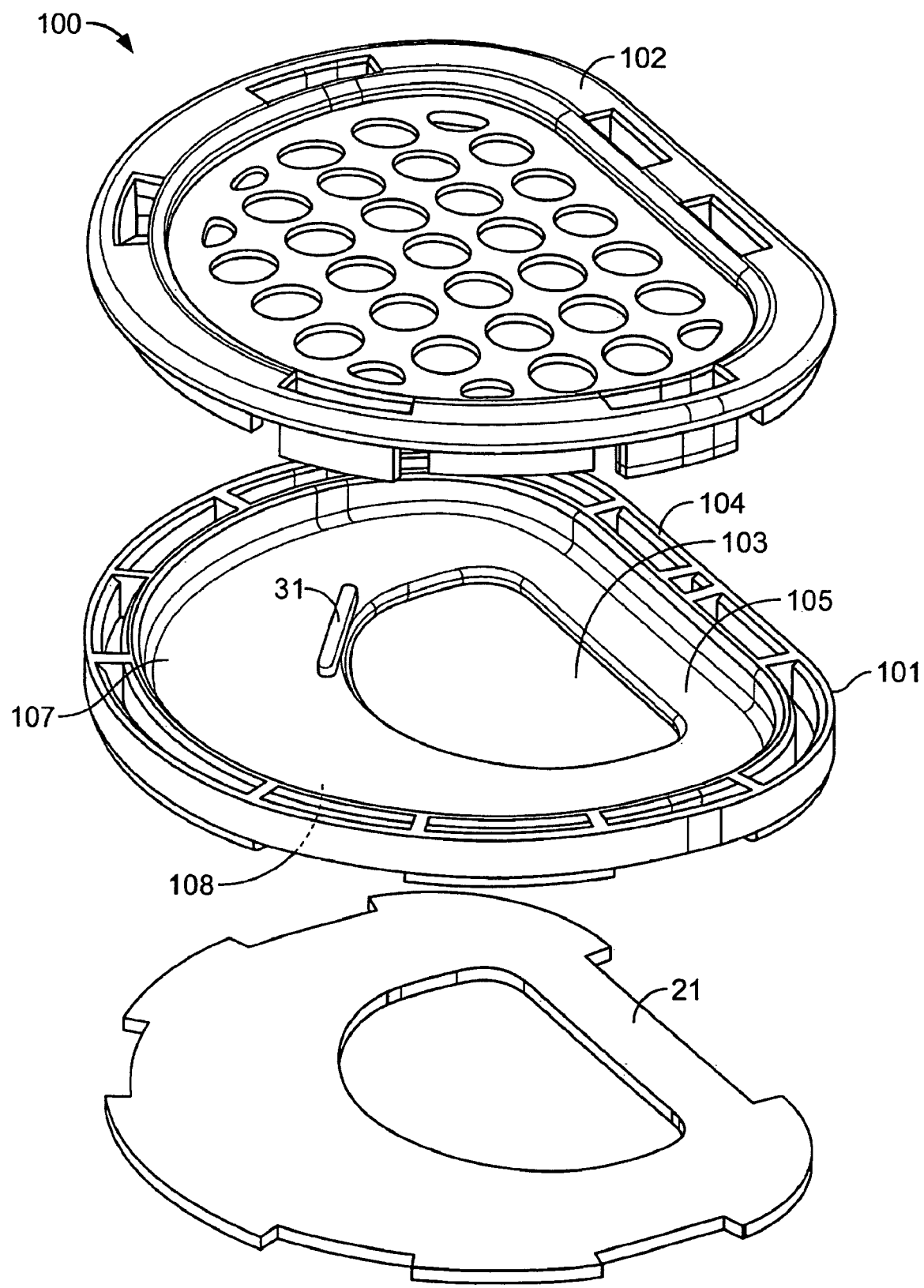
FIG. 10B is an exploded view of the clam shell with a top section having a rim bounding a surface having a plurality of holes.
Figure 10C:
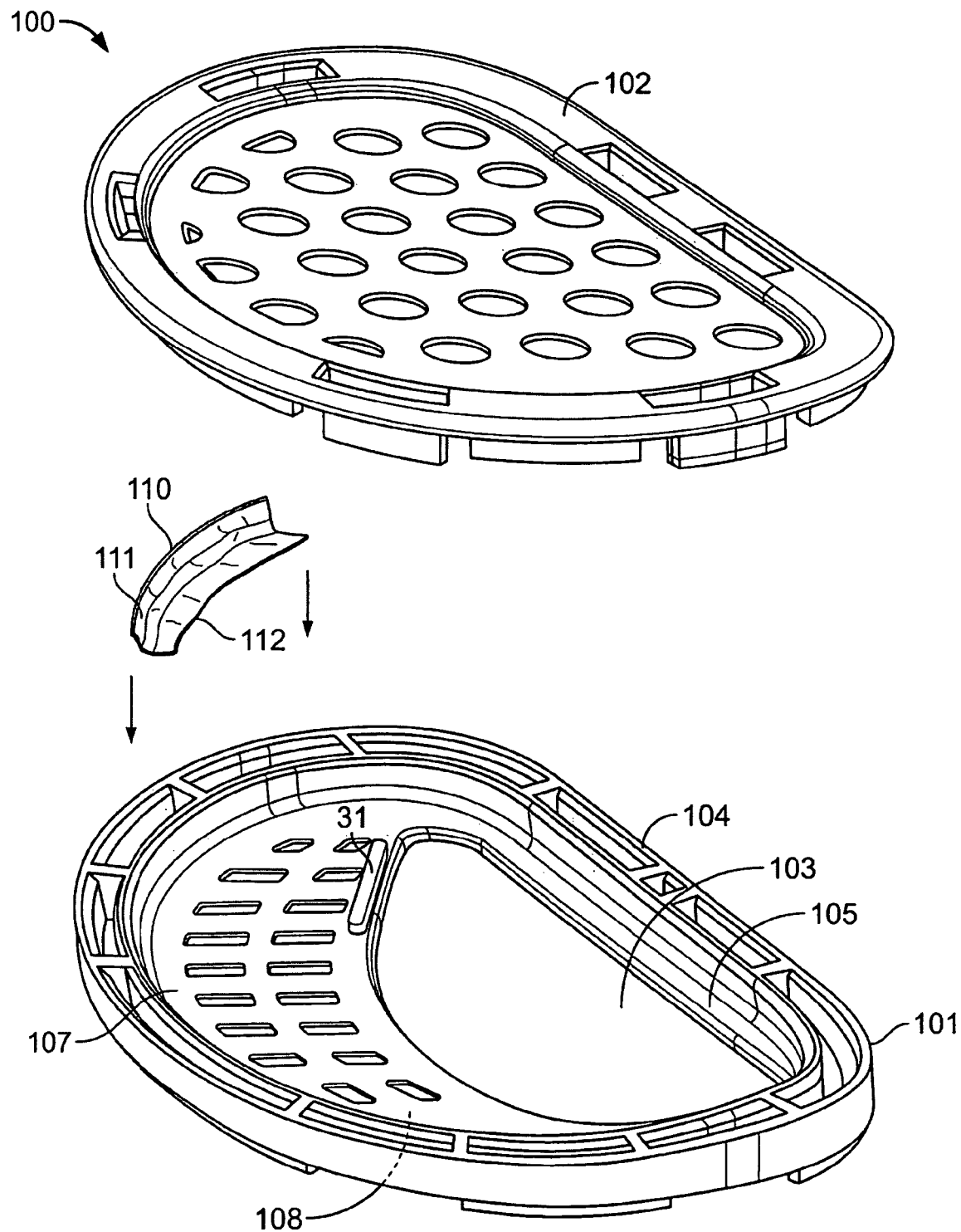
FIG. 10C is an exploded view of the clam shell with the posterior stint formed integrally with the bottom section and showing a biocompatible strip of material positioned on the anterior surface of the bottom section.

As shown in FIGS. 10A-C, instead of using a single adhesive element, a clam shell can be used to hold the stints in a desired position to correct the deformity. The clam shell also provides pressure on the conchal stint, if present, helping to correct the conchal deformity. The clam shell can be made out of a biocompatible polymer such as polypropylene.

FIG. 10A-10C show a view of clam shell 100 in an exploded configuration. Clam shell 100 has a housing 101, which has a base section 105, including a rim 104 permanently attached to or formed continuous with the base section 105, and a cap or top section 102 that releasably engages with the base section. Alternatively, rim 104 can be positioned on the cap 102 or on both the base section and the cap such that there is a rim section when the base section and the cap are releasably engaged. Base section 105 has an opening 103 through which the ear is inserted for correction of a deformity. The base section 105 has an anterior surface 107, upon which the pinna of the ear rests after being inserted through opening 103, and a posterior surface 108. The base section can have one or more passages through the anterior to the posterior surface allowing the skin beneath the base section 105 to breath. In some implementations, at least a portion of posterior surface 108 can be covered with an adhesive allowing placement of the posterior surface 108 on the retroauricular skin surface 18 (eliminating the need for the double adhesive element 21). The adhesive can be covered by a peel-off material applied over the adhesive to prevent the posterior surface from adhering to other surfaces prior to placement on the retroauricular skin surface 18. This peel-off material can be removed prior to application to the retroauricular skin surface 18. In other implementations, there is no adhesive on the posterior surface 108. The double adhesive element 21 can be used to adhere the clam shell onto the retroauricular skin surface. The double adhesive element can be shaped to conform to the shape of the base section with one adhesive surface adhered to the posterior surface 108 of the base section and the other adhesive surface adhered to the retroauricular skin surface.

In some implementations, at least a portion of the anterior surface 107 can be coated with an adhesive (with or without a peel-off material covering the adhesive) or a strip of biocompatible material 110 having a posterior adhesive surface 112 adhered to the anterior surface 107, and a anterior adhesive surface 111. The posterior stint 31 can be applied directly onto the adhesive or the anterior adhesive surface 111, which holds the stint in place. The adhesive can also be used to tack the ear down when it is rolled out over the posterior stint 31. In some implementations, there is no adhesive on the anterior surface 107. In other implementations, as shown in FIG. 10C, a posterior stint 31 can be molded directly on the anterior surface 107 in a position to maintain a desired anatomic shape of the ear in an area of the antihelix and the superior limb of the triangular fossa and the adhesive or anterior adhesive surface 111 is used to tack the ear down over the posterior stint 31.

The cap 102, which can be a solid cap or, as seen in FIGS. 10B and 10C, a rim (which articulates or releasably engages with the rim of the base section) bounding a surface having a plurality of holes (or a mesh) that overlies the ear. In some implementations the cap is made as a single unit and holes are molded and/or punched in the cap to form the surface having a plurality of holes. In other implementations, the mesh can be formed separately and attached to the rim by radio frequency (RF) or ultrasonic welding. The holes in the surface/mesh allows the ear to be visualized when the clam shell is closed to check position of the stint(s) and/or to check the ear for points where to much pressure is being applied.

The cap 102 is reversibly or releasably attachable to base section 105 such that base section 105 and cap 102, when attached, form a compartment into which the ear 1 can be placed to correct a deformity. The cap applies stabilizing pressure to the ear and the stints. The cap can be attached to the base section by any reversible attachment mechanism such as two or more snaps, or a hinge and one or more snaps, or hook and loop fasteners, or lug and notch, or a latch type mechanism, or any other type of fastening mechanism that securely and reversibly attaches the cap to the base section.

To correct an ear deformity, the ear 1 is passed through opening 103. At least a portion of a posterior surface of the base section 105 is adhered to the retroauricular skin surface 18. Either an adhesive on the posterior surface 108 can be used to adhere the base section 105 to the retroauricular skin surface or the base section 105 can be placed on the second adhesive surface 27 of the double adhesive element 21 that can be located on the retroauricular skin 18 and sized and shaped to fit the posterior surface 108.

Once the base section 105 is attached to the retroauricular skin surface 18 with the ear positioned inside of the clam shell, the posterior stint is positioned, if necessary, when there is a malformed or missing superior crus. This can include using a clam shell with the posterior stint molded on the anterior surface 107 in a position located to correct the shape of the ear the area of the superior crus 17, or using an anterior surface 107 with an adhesive or the anterior adhesive surface 111 to tack the posterior stint 31 in place, or positioning a posterior stint (which can have a tacky surface) on the anterior surface 107, which does not have an adhesive thereon. The ear is rolled out over the anterior surface 107 of the base section 105 and the posterior stint 31 and tacked down to the adhesive or the anterior adhesive surface 111 (if necessary). The anterior stint 32 is placed in the scaphoid fossa (if necessary), and the conchal stint 71 in the concha (if necessary). Then, the cap 102 is snapped into a closed position applying a desired amount of pressure to maintain the ear 1 and splints/stints/ stents in the desired positions. As the cap 102 is closed, in addition to holding the splints in place, the cap compresses the conchal stint, such that molding and shaping of the pinna and concha occurs. This permits flattening of the conchal crus by the selective force created by the stint and clam shell. In some implementations, a strip of tape may be additionally applied to hold the scaphal splint 32 in place.

In other implementations, a compressible media 106, such as foam or a bladder or a gel, can be placed between the ear and the cap 102, allowing the cap 102 to exert the desired amount of pressure on the foam/bladder/gel to hold the ear and splints in the desired position. As the cap 102 is closed, in addition to holding the splints in place, the interposed foam/bladder/gel is compressed against the conchal stint, such that molding and shaping of the pinna and concha occurs. This permits flattening of the conchal crus by the selective force created by the stint and clam shell. The foam can be made out of a biocompatible material, such as polyethylene and can be sized and shaped to apply a desired amount of pressure to chosen portions of the ear and/or stints.

Figure 9:
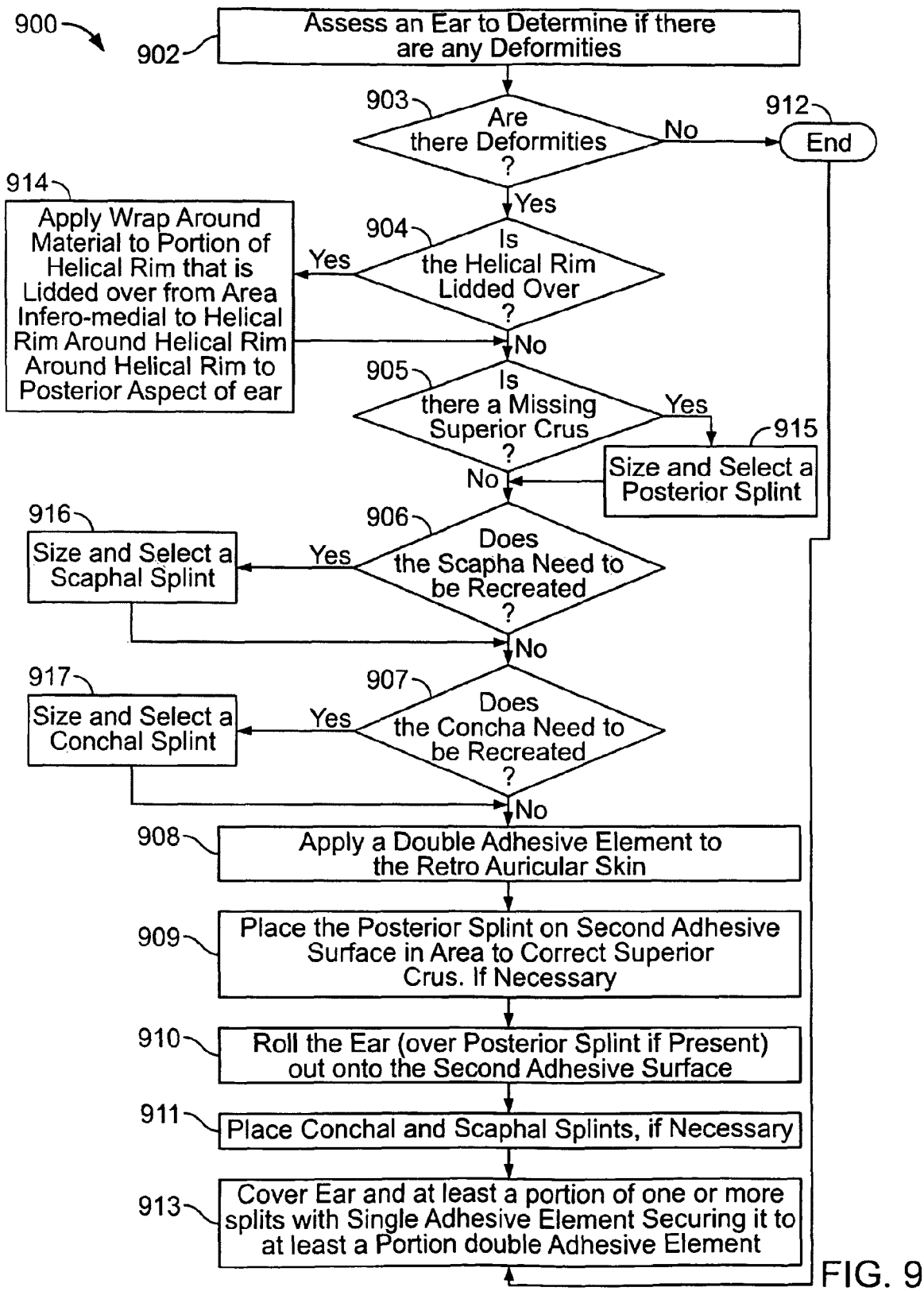
FIG. 9 is a flow diagram depicting one implementation of a method of correcting a misshaped ear.

As shown in FIG. 9, one implementation of process 900 of correcting a misshaped ear 1 begins with an assessment 902 of the ear. The process involves a visualization of deformities and correction thereof. Although steps of the process 900 are recited in a particular order, one or more steps can be performed in a different order to achieve desired results. A determination 903 that there are not any deformities results in the process ending. However, if a determination 903 is positive for one or more deformities, then a determination 904 is made as to whether an area of helical rim 11 is lidded over. If the helical rim is lidded over, then a wrap-around material 61 is applied 914 from an area infero-medial to the lidded over area of the helical rim around the helical rim 11 to a posterior aspect of the ear. Either after the wrap-around material has been placed or after a negative determination for an area of lidding over of the helical rim, the process proceeds to a determination 905 as to whether there is a missing or deformed superior crus 17. If there is a positive determination 905 for the missing or deformed superior crus 17, then a posterior splint 31 is selected 915 having an appropriate size and shape for correction thereof.

Following a negative determination 905 or the selection 915 of the posterior splint 31, a determination 906 is made as to whether an area of the scapha 12 needs to be recreated. A positive determination 906 that the scapha needs to be recreated results in a selection 916 of a scaphal splint 32 of an appropriate size and shape. Then, the process proceeds, as it would with a negative determination 906, to a determination 907 as to whether an area of the concha 13 needs to be recreated. A positive determination results in a selection 917 of a conchal splint 71 of an appropriate size and shape.

Once the determination as to the appropriate size and shape of splints has been made, a first adhesive surface 26 of a double adhesive element 21 is applied 908 to an area of retroauricular skin 18. The selected posterior splint 31 is placed 909 on a second adhesive surface 27 of the double adhesive element 21 in an area where the superior crus is to be recreated. The ear 1, including the ear lobe 9, if deformed, is rolled out 910 over the second adhesive surface 27 with the posterior splint 31 in between the two. Then, if necessary, the scaphal splint 32 is placed 911 in an area of the scapha that needs to be recreated taking care not to cross over the posterior splint 31 in area 51. Also, the conchal splint 71, if necessary, is placed in an area of the concha 13 that needs to be recreated. In some implementations, a single adhesive element then covers 913 at least a portion of one or more of the scaphal and conchal splints, if present, and of the second adhesive surface 27.

In other implementations, a clam shell 100 can be used. If a clam shell is used, then process 900 proceeds as described above until applying 908 of the double adhesive element 21 to the retroauricular skin. Instead, the ear is positioned within the clam shell, which is placed 909 on the second adhesive surface 27 (or, if the posterior surface 108 has an adhesive, the posterior surface is applied directly onto the retroauricular skin surface 18) and the posterior splint 31 is placed (in some implementations already present) on the anterior surface 107 of the base section 105 in an area to recreate the superior crus. The process continues with the scaphal splint 32 and conchal splint 71, if necessary, being placed 911 in the desired position to correct the deformity. Then, closing 913 the cap of the clam shell to secure the splints in place and apply a desire amount of pressure on the conchal splint, if present.

When correcting the shape of the misshaped ear, the duration of treatment with the above described system depends on the age of the infant or neonate at the time of diagnosis. An earlier diagnosis will shorten the duration of treatment, for example when treatment begins at about 1 week of age, the duration of the treatment is in the range of 6 to 8 weeks. However, if the diagnosis is not made until 3 weeks of age, then the duration of treatment is in the range of 4 to 6 months.

The system can be used with deformities having minimal soft tissue and/or cartilage deficiency, and with deformities having greater cartilage deficiency, such as Tanzer II. Examples of deformities where the system can be used are as follows: prominent ear, cup ear, lop ear, Stahl's ear, conchal crus, misshapen ears, helical rim compression, Tanzer I-II constricted ear, and prominent ear lobule. The following paragraphs describe examples of how the components of the system can be used to treat various ear deformities. In other implementations, the clam shell 100 can be used to treat the various ear deformities.

For example, in Stahl's ear, the system can be used to correct an abnormal transverse crus through a portion of the scapha 12, an absent superior crus 17, and lidding over of the helical rim. The posterior splint 31 is used to correct the missing superior crus 17, and the anterior scaphal splint 32 is used to correct the shape of the scapha 12. Although application of the components is recited in a particular order, other orders of application can be used as long as the interaction of the components is maintained.

Although not necessary, if desired, an alcohol swab can be used to wipe off any excess oil on the skin covering the front and back of the ear, allowing the adhesive to stick more easily to the skin. Also, if desired, an application of a liquid adhesive, such as tincture of benzoin or MASTISOL™, to the skin can be used to further aid in adhesion of the system components to the skin of the ear and retroauricular area. An appropriately sized posterior splint 31 is selected, such that it essentially extends from the antihelix to the helical rim, as shown in FIGS. 4A-4B, and an appropriately sized anterior scaphal splint 32 is selected, such that it crosses the abnormal transverse crus, but does not extend over the posterior splint in area 51, as shown in FIGS. 8A-8B. Then, the wrap-around material 61 is applied to the portion of the helical rim 11 that is lidded over. The wrap-around material 61 is applied first to an area infero-medial to the helical rim on the interior portion of the helix then wrapped around the helical rim and secured to the skin on the posterior aspect of the ear.

Referring to FIGS. 4 and 8, with the ear pulled up, the double adhesive element 21 is applied to the retroauricular skin surface 18 behind/posterior to the ear, after removing the first adhesive cover 24. The second adhesive cover 25 is removed and the posterior splint 31 is attached to the second adhesive surface 27 in a desired position, such that the correct anatomic shape of the superior crus of the antihelix 17 is created, i.e. essentially from the antihelix to the helical rim. The ear 1 is rolled out and applied or tacked down to the second adhesive surface 27. The anterior splint 32 is applied in the area of the scapha 12, avoiding an overlap between the posterior splint 31 and the anterior splint 32. Then, the anterior splint 32 and the ear 1 are further secured in position with the single adhesive element 81 (see FIG. 8), after removing the single adhesive cover 83. The single adhesive element 81 overlays the ear, the other ear molding components, including the exposed portion of the second adhesive surface 27, thus providing a cover and a degree of protection for the ear molding components from the prying hands of an infant or neonate.

For an infant or neonate who has a scaphal deformity, the ear is treated just like a Stahl's ear, but no wrap-around material is used.

For lop ear deformity (and lidding, a less severe form of lop ear) where the helix is hooded or lidded over, the wrap-around material 61 is wrapped around the helix in the hooded area to expand the skin. The double adhesive element 21 is applied to the retroauricular skin surface 18, and the posterior splint 31 is positioned on the second adhesive surface 27 in a desired location. Then, the ear is tacked down on the second adhesive surface 27 with the lidded over portion being rolled out. The anterior splint 32 is placed in the scapha, making sure that there is no overlap in area 51 with the posterior splint 31. Then, the single adhesive element 81 is applied covering the ear and splint components.

Tanzer I and II appear like lop ear, but there is a deficiency of skin (Tanzer I and II) and cartilage (Tanzer II) on the inner surface of the helical rim that prohibits rolling the rim out. The double adhesive element 21 is applied to the retroauricular skin surface 18. Wrap-around material 61 is applied to the lidded over portion of the ear, and then the ear is rolled out onto the second adhesive surface 27 of the double adhesive element 21. This stretches the deficient inner skin of the helical rim. Tanzer II constricted ears may end up smaller due to the cartilage deficiency, but with acceptable shape. Then, the single adhesive element is applied to cover the ear and other splint components if necessary. For helical rim compression, in which the ears are crumpled and not fully unfolded in utero, the double adhesive element 21 is applied to the retroauricular skin surface 18 and the ear is expanded out onto the second adhesive surface 27. The anterior splint 32 is applied to the area of the scapha 12 and then the single adhesive element 81 is applied to secure the anterior adhesive splint 32, covering the ear and the double adhesive element that remains exposed after tacking the ear down.

For cup ears, which stick out too far and are characterized by incomplete curvature or formation of the antihelix and superior limb of the triangular fossa, and which have over development of the vertical wall of the concha, the double adhesive element 21 is applied to the retroauricular skin surface 18. The ear is then tacked down onto the second adhesive surface 27. A conchal stint 71 is applied to the concha 13 of the ear. The single adhesive element 81 covers the conchal stint 71, the ear, and the exposed portion of the second adhesive surface 27.

For prominent lobule, the double adhesive element 21 can be used to roll the ear, including the lobule 9, out and tack it down to the second adhesive surface 27.

A number of implementations have been described. Nevertheless, it will be understood that various modifications may be made. For example, one or more stints may or may not be used depending on the ear anatomy needing correction. Different types of adhesives/tapes can be used to secure the ear and stint into their desired positions. Accordingly, other implementations are within the scope of the following claims.

What is claimed is:

1. A molding device for a human ear comprising:
a base section defining an opening dimensioned to accommodate the passage of the ear through the opening, wherein the ear includes an antihelix, a superior limb of the triangular fossa, a helix, helical rim, a base, a concha, and a scaphal area, and the base section includes a posterior surface and an anterior surface;
a top section releasably engageable with the base section defining a compartment therebetween; and
a posterior stint arranged on the anterior surface constructed to maintain a desired anatomic shape of the ear in an area of the antihelix and the superior limb of the triangular fossa.

2. The molding device of claim 1, wherein the posterior stint is integrally formed with the base section.

3. The molding device of claim 1 comprising a strip of biocompatible material having a first adhesive surface and a second adhesive surface, the strip shaped to facilitate placement of the first adhesive surface of the strip on the anterior surface of the base section in a position to facilitate placement of an area of skin on a posterior aspect of the ear between the base of the ear and the helical rim over the posterior stint and on the second adhesive surface of the strip.

4. The molding device of claim 1 comprising an anterior stint adapted for placement in the scaphal area of the ear, the anterior stint further constructed to maintain a desired contour of the scaphal area.

5. The molding device of claim 4 wherein the top section is adapted to apply a stabilizing pressure to the ear, the posterior stint, and the anterior stint.

6. The molding device of claim 4 comprising a tacky surface on the anterior stint.

7. The molding device of claim 1 comprising a conchal stint adapted for placement in the concha of the ear to maintain a desired anatomic shape of the concha.

8. The molding device of claim 7, wherein the conchal stint comprises a half-moon shape configured for placement around a back wall of the concha, such that pressure applied by the top section facilitates maintenance of the desired anatomic shape of the concha.

9. The molding device of claim 8 comprising a cap constructed for positioning between the conchal stint and the top section, wherein the cap is configured in combination with the top section to provide a stabilizing pressure to the conchal stint.

10. The molding device of claim 1 further comprising a biocompatible wrap-around material, having a single adhesive surface, configured such that a first end of the wrap-around material can be positioned using the single adhesive surface on the ear in an area infero-medial to the helical rim, such that the wrap-around material can be wrapped around the helix, and such that a second end of the wrap-around material can be secured to skin on a posterior aspect of the ear to expand the skin in the infero-medial area.

11. The molding device of claim 1 comprising an adhesive material on the posterior surface of the base section configured to adhere the posterior surface to a retroauricular skin surface.

12. The molding device of claim 1 further comprising a biocompatible material having a first adhesive surface and a second adhesive surface, the biocompatible material shaped to facilitate placement of the first adhesive surface of the biocompatible material posterior to the ear on a retroauricular skin surface and placement of the posterior surface on the second adhesive surface of the biocompatible material.

* * * * *